United States Patent
Sakurai et al.

(10) Patent No.: US 8,378,148 B2
(45) Date of Patent: Feb. 19, 2013

(54) ALCOHOLIC HYDROXYL-CONTAINING COMPOUNDS AND MAKING METHOD

(75) Inventors: Takato Sakurai, Annaka (JP); Michihiro Sugo, Annaka (JP); Takanobu Takeda, Annaka (JP); Hideto Kato, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 338 days.

(21) Appl. No.: 12/898,136

(22) Filed: Oct. 5, 2010

(65) Prior Publication Data

US 2011/0082321 A1    Apr. 7, 2011

(30) Foreign Application Priority Data

Oct. 6, 2009   (JP) .................. 2009-232294

(51) Int. Cl.
 *C07C 43/23* (2006.01)
 *C07C 41/26* (2006.01)
(52) U.S. Cl. ...................... 568/640; 568/641
(58) Field of Classification Search .................. None
 See application file for complete search history.

(56) References Cited

U.S. PATENT DOCUMENTS

| 4,433,179 A * | 2/1984 | Lohse et al. ............. 568/664 |
| 5,070,117 A * | 12/1991 | Klemarczyk et al. ........ 522/31 |
| 6,001,954 A * | 12/1999 | Smits et al. ............. 528/219 |

FOREIGN PATENT DOCUMENTS

| JP | 8-12745 A | 1/1996 |
| JP | 8-67805 A | 3/1996 |
| WO | WO 2005/037755 A2 | 4/2005 |
| WO | WO 2010/000066 A1 | 1/2010 |

OTHER PUBLICATIONS

European Search Report issued Apr. 5, 2011, in European Patent Application No. 10 25 1748.

Mou et al., "Synthesis of a hydrophilic phosphonic acid monomer for dental materials," Chem. Commun., Jan. 25, 2000, vol. 5, pp. 345-346.

Pala et al., "New Phenolic Ethers. I. Synthesis and Pharmacology of Alpha-glyceryl Ethers of Methylene-bis-phenols," Farmaco, Edizione Scientifica, Societa Chimica Italiana, Pavia, IT, Sep. 1, 1963, vol. 18, No. 9, pp. 619-642.

Satoh et al., "Study on anti-androgenic effects of bisphenol a diglycidyl ether (BADGE), bisphenol F diglycidyl ether (EFDGE) and their derivatives using cells . . . ,"Food and Chemical Toxicology, Feb. 7, 2004, vol. 42, No. 6, pp. 983-993.

* cited by examiner

*Primary Examiner* — Rosalynd Keys
(74) *Attorney, Agent, or Firm* — Birch, Stewart, Kolasch & Birch, LLP

(57) ABSTRACT

Bisphenol derivatives having both alcoholic hydroxyl and allyl groups are novel and useful as reagents for modifying organic resins and silicone resins.

2 Claims, 2 Drawing Sheets

ALCOHOLIC HYDROXYL-CONTAINING COMPOUNDS AND MAKING METHOD

CROSS-REFERENCE TO RELATED APPLICATION

This non-provisional application claims priority under 35 U.S.C. §119(a) on Patent Application No. 2009-232294 filed in Japan on Oct. 6, 2009, the entire contents of which are hereby incorporated by reference.

TECHNICAL FIELD

This invention relates to novel alcoholic hydroxyl-containing compounds which are useful as reagents for modifying organic resins and silicone resins in electronic applications, and a method for preparing the same.

BACKGROUND ART

Alcoholic hydroxyl-containing bisphenol derivatives are known in the art and include, for example, those of the general formula (4):

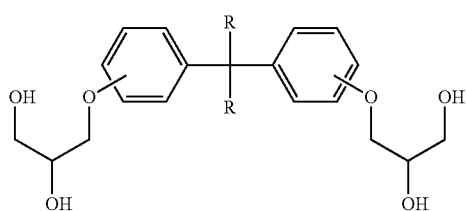

(4)

wherein R is hydrogen, methyl or trifluoromethyl. The possession of alcoholic hydroxyl groups allows for functionality conversion to introduce new functional groups and hence to impart new properties. When polymerization or modification of such bisphenol derivatives is considered, it is desirable from the standpoints of properties and reactivity that the derivatives have an allyl group. However, bisphenol compounds having both an allyl group and a glycerol group substituted on an aromatic ring are unknown.

JP-A H08-12745 and JP-A H08-67805 disclose the use of allylated bisphenols as the curing agent in epoxy resin compositions. Although allylated bisphenols are useful as the curing agent in epoxy resin compositions, they are unsuited to modify silicone and other resins.

Citation List
Patent Document 1: JP-A H08-12745
Patent Document 2: JP-A H08-67805

DISCLOSURE OF INVENTION

An object of the invention is to provide novel bisphenols having both alcoholic hydroxyl and allyl groups which are useful as reagents for modifying organic resins and silicone resins, and a method for preparing the same.

In one aspect, the invention provides an alcoholic hydroxyl-containing compound having the general formula (1):

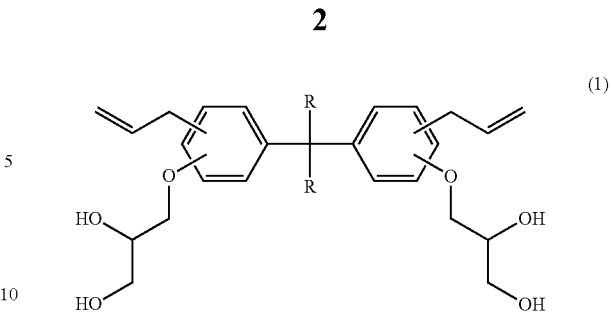

(1)

wherein R is hydrogen, methyl or trifluoromethyl.

Another aspect of the invention provides a method for preparing the alcoholic hydroxyl-containing compound of formula (1). The compound of formula (1) is prepared by reacting a bisphenol derivative of the general formula (2) with water in the presence of a transition metal catalyst of the general formula (3).

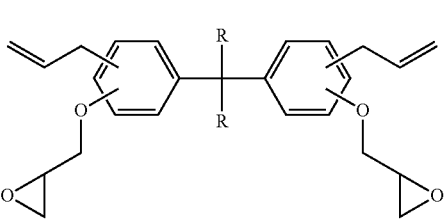

(2)

Herein R is hydrogen, methyl or trifluoromethyl.

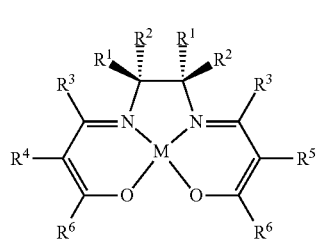

(3)

Herein $R^1$ and $R^2$ are hydrogen, alkyl or aryl, may have a substituent, or two $R^1$ or two $R^2$ may bond together to form a ring with the carbon atoms to which they are attached; $R^3$, $R^4$, $R^5$ and $R^6$ are hydrogen, alkyl or aryl, $R^4$ and $R^5$ may also be a polymer like hydroxymethylpolystyrene or silica gel, $R^6$ may form an optionally substituted ring with adjacent $R^4$ or $R^5$ and the carbon atoms to which they are attached; and M is manganese, iron, cobalt, zinc, nickel, aluminum, chromium, ruthenium, rhodium, titanium, vanadium, molybdenum, or tungsten.

ADVANTAGEOUS EFFECTS OF INVENTION

The alcoholic hydroxyl-containing compounds are novel and useful as reagents for modifying organic resins and silicone resins. The method is successful in preparing the alcoholic hydroxyl-containing compounds in high yields.

DESCRIPTION OF EMBODIMENTS

Figure 1:
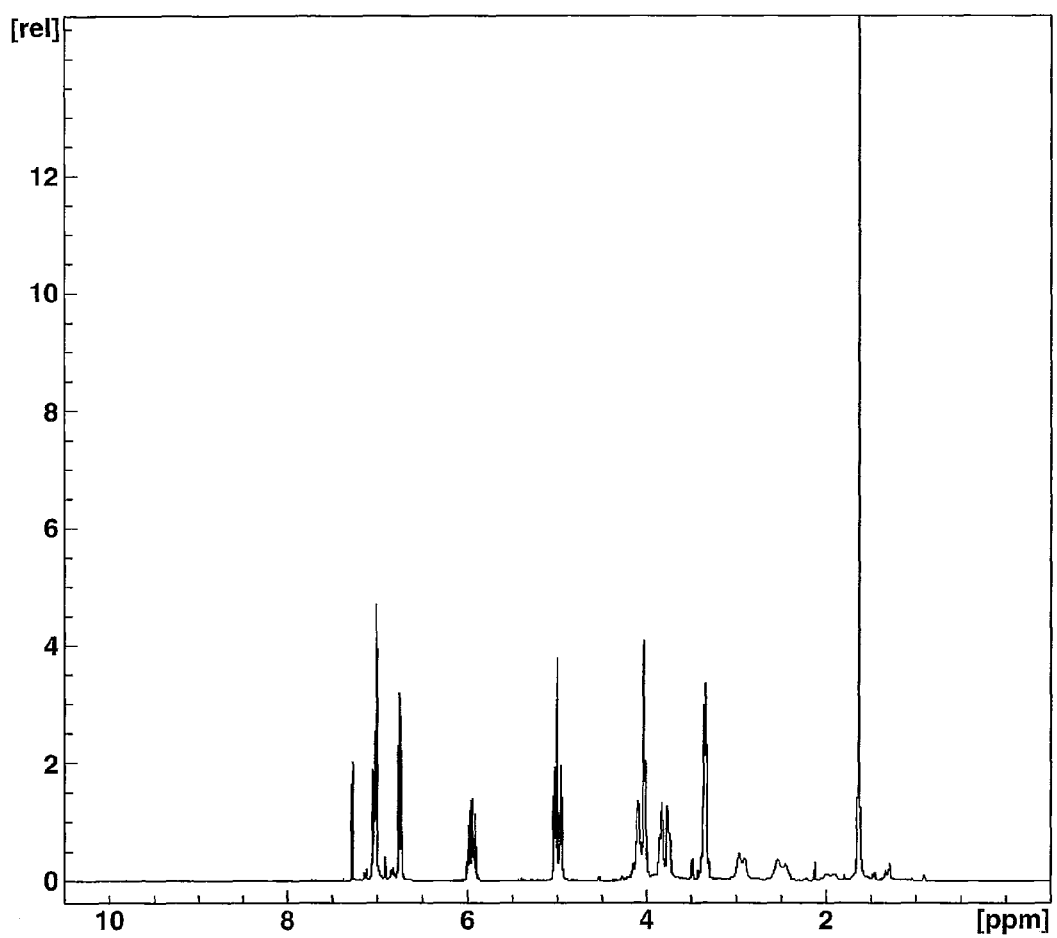
FIGS. 1 and 2 are $^1$H-NMR and $^{13}$C-NMR diagrams of the alcoholic hydroxyl-containing compound in Example 1, respectively.

The invention provides an alcoholic hydroxyl-containing compound having the general formula (1):

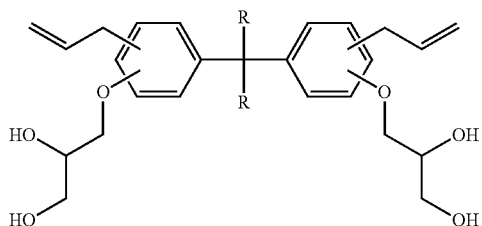
(1)

wherein R is hydrogen, methyl or trifluoromethyl.

Illustrative examples of the alcoholic hydroxyl-containing compound of formula (1) are given below.

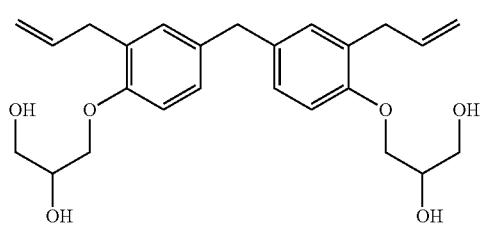

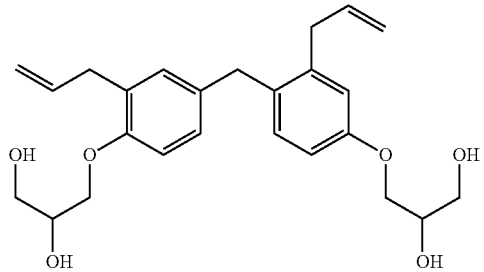

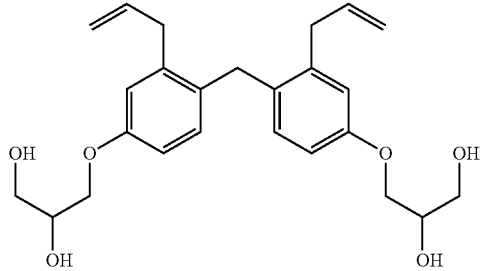

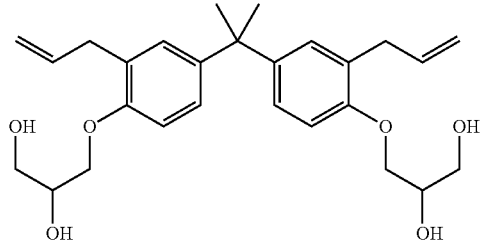

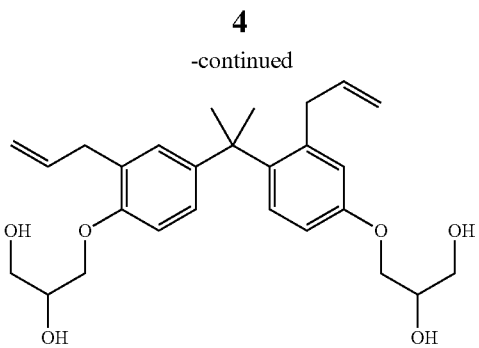

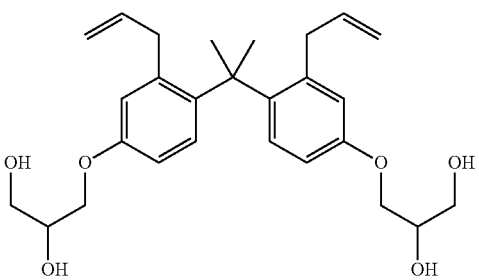

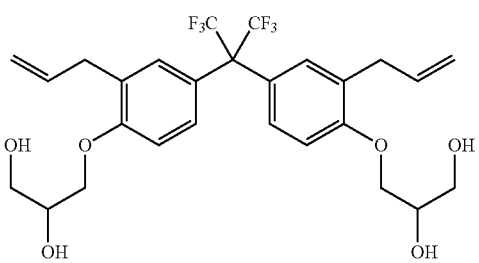

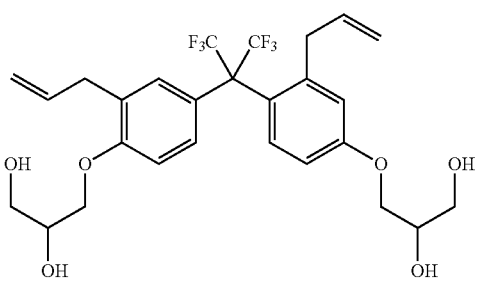

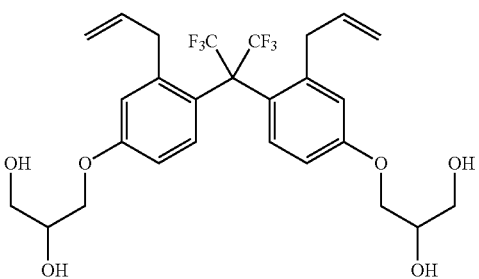

Also the invention provides a method for preparing the alcoholic hydroxyl-containing compound of formula (1) by reacting an epoxy-containing bisphenol derivative of the general formula (2) with water in the presence of a transition metal catalyst of the general formula (3).

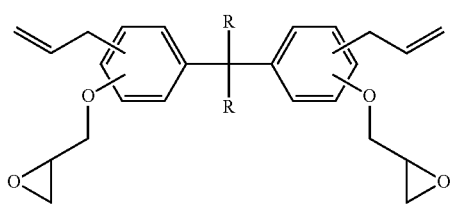

(2)

Herein R is hydrogen, methyl or trifluoromethyl.

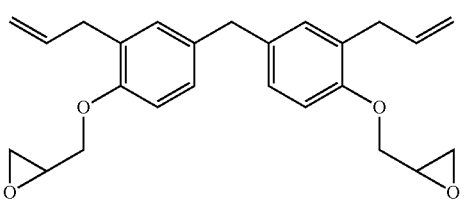

(3)

Herein $R^1$ and $R^2$ are hydrogen, alkyl or aryl, may have a substituent(s), or two $R^1$ or two $R^2$ may bond together to form a ring with the carbon atoms to which they are attached. $R^3$, $R^4$, $R^5$ and $R^6$ are hydrogen, alkyl or aryl, $R^4$ and $R^5$ may also be a polymer like hydroxymethylpolystyrene or silica gel, $R^6$ may form an optionally substituted ring with adjacent $R^4$ or $R^5$ and the carbon atoms to which they are attached. M is manganese, iron, cobalt, zinc, nickel, aluminum, chromium, ruthenium, rhodium, titanium, vanadium, molybdenum, or tungsten.

The reaction proceeds according to the following scheme.

Herein R, $R^1$ to $R^6$ and M are as defined above.

Illustrative examples of the bisphenol derivative of formula (2) are given below.

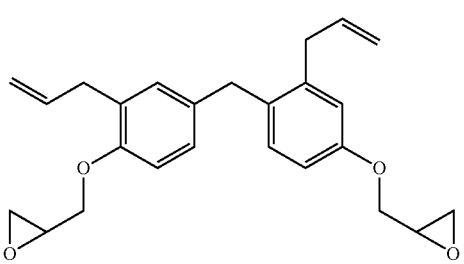

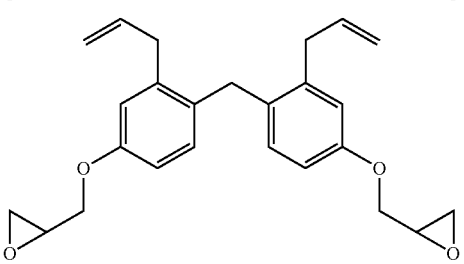

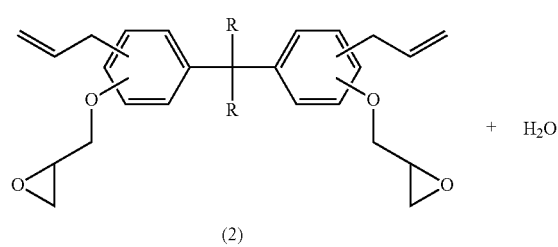 + $H_2O$ 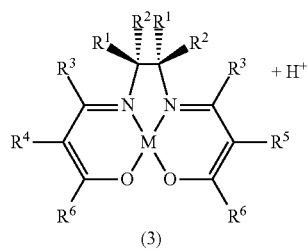

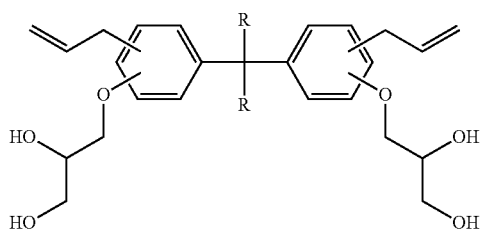

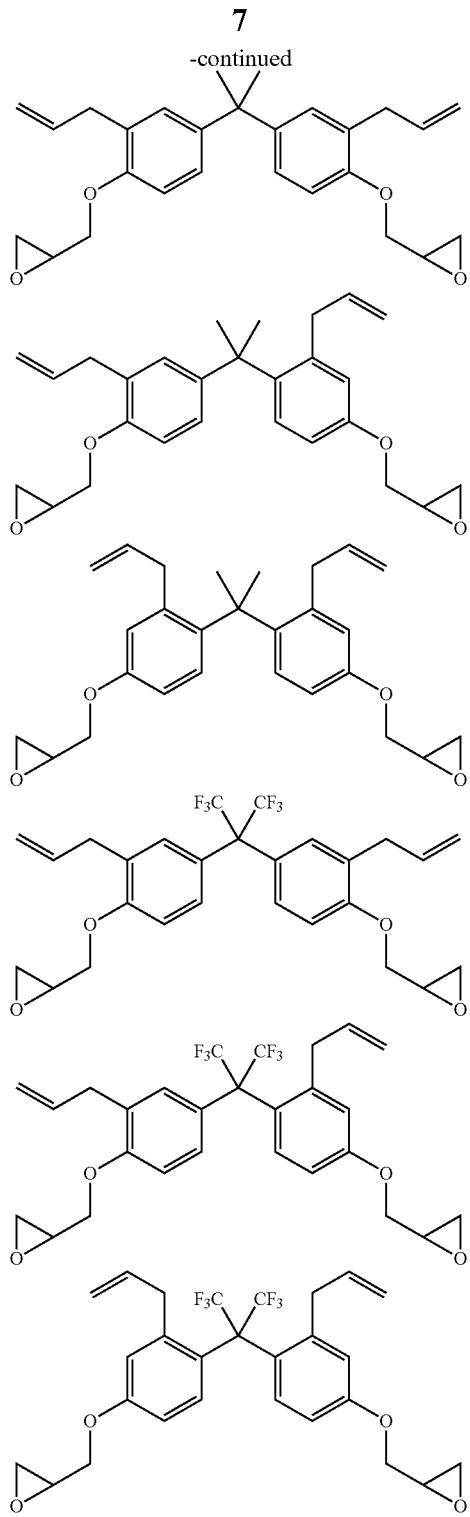

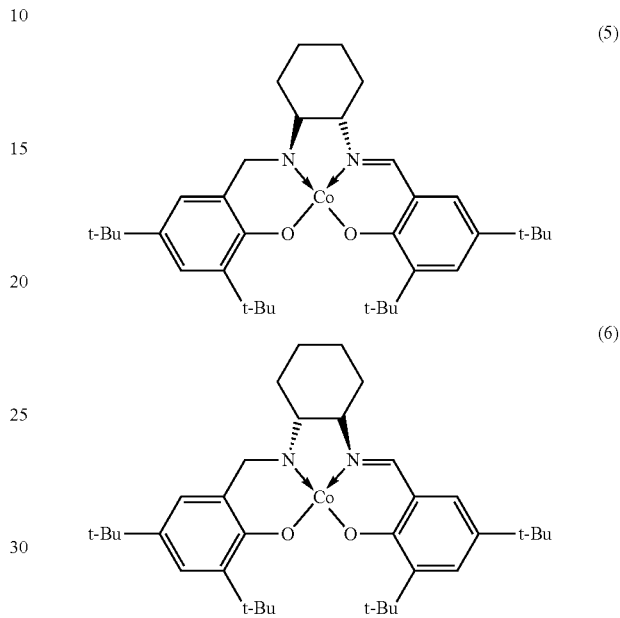

The metal complexes used herein are well known in the art and are represented by the general formula (3). The center metal M is not particularly limited. Typical metals include manganese, iron, cobalt, zinc, nickel, aluminum, chromium, ruthenium, rhodium, titanium, vanadium, molybdenum, and tungsten, with cobalt being most suitable in the method. Likewise, $R^1$, $R^2$, $R^3$, $R^4$, $R^5$, and $R^6$ in formula (3) are not particularly limited. In a preferred embodiment, $R^1$ and $R^2$ are hydrogen, alkyl or aryl. $R^1$ and $R^2$ may have one or more substituents such as alkyl or aryl. Also, two $R^1$ or two $R^2$ may bond together to form a ring with the carbon atoms to which they are attached. Suitable rings include saturated non-aromatic rings of 3 to 20 carbon atoms. $R^3$, $R^4$, $R^5$ and $R^6$ are hydrogen, alkyl or aryl. $R^4$ and $R^5$ may also be a polymer like hydroxymethylpolystyrene or silica gel. $R^6$ may form a ring of 3 to 20 carbon atoms with adjacent $R^4$ or $R^5$ and the carbon atoms to which they are attached, and the ring may have one or more substituents such as alkyl or aryl.

The preferred catalysts are those of formulae (5) and (6).

Herein t-Bu stands for tert-butyl.

Since the catalysts of formulae (5) and (6) are asymmetric, the reaction rate differs with the configuration of epoxy in the substrate. It is then preferred to use the metal catalyst as a combination of enantiomers.

The catalyst of formula (3), (5) or (6) is activated through air oxidation from n-valence to (n+1)-valence with air and an acid, preferably an organic acid. In a preferred embodiment of the method, an acid, typically an organic acid is used along with the catalyst. Suitable organic acids are compounds having an acidic functional group such as carboxylic acids, sulfonic acids, sulfinic acids, and phenols and include, for example, aliphatic carboxylic acids of 1 to 10 carbon atoms, aromatic carboxylic acids of 7 to 20 carbon atoms, aliphatic sulfonic acids of 1 to 10 carbon atoms, aromatic sulfonic acids of 6 to 20 carbon atoms, aliphatic sulfinic acids of 1 to 10 carbon atoms, and aromatic sulfinic acids of 6 to 20 carbon atoms. Specific examples include acetic acid, propionic acid, p-toluenesulfonic acid, and methanesulfonic acid. Aliphatic carboxylic acids of 1 to 5 carbon atoms are preferred, with acetic acid being most preferred. From the standpoints of catalyst stability, activity and reproducibility, it is ideal to use the catalyst as activated with these acids.

An appropriate amount of the catalyst used is 0.01 to 10.0 mol %, more preferably 0.05 to 5.0 mol %, even more preferably 0.15 to 1.5 mol %, and most preferably 0.25 to 0.75 mol %, based on the bisphenol derivative of formula (2). Too small an amount of the catalyst may lead to a decline of reaction rate whereas an excess amount may increase the cost of manufacture despite a shortened reaction time. The acid is preferably used in such amounts as to give a molar ratio of acid to catalyst of from 0.1 to 15.0, more preferably 1.0 to 10.0, even more preferably 2.0 to 8.0, and most preferably 4.0 to 6.0. An excess of the catalyst may promote decomposition of the catalyst.

In the method of the invention, a solvent is preferably used. Although the amount of the solvent used is not particularly limited, it is generally used in an amount of 10 to 1,000 mL, preferably 50 to 500 mL, more preferably 80 to 250 mL, and even more preferably 100 to 140 mL, per mole of the bisphenol derivative of formula (2). The solvent used herein is not particularly limited as long as it is compatible with the epoxy-containing bisphenol derivative and the metal catalyst. Suitable solvents include ketones such as acetone and methyl ethyl ketone, ether solvents such as diethyl ether, tetrahydrofuran, and 1,4-dioxane, and organic solvents such as toluene, xylene, and hexane, which may be used alone or in combination of two or more. Preferred are ether solvents, with tetrahydrofuran being most preferred.

Another reactant is water which is preferably used in such amounts as to give a molar ratio of water to epoxy-containing bisphenol of from 1.0 to 15.0, more preferably 1.4 to 10.0, even more preferably 1.8 to 5.0, and most preferably 2.2 to 3.0. It is recommended that the reaction temperature be in a range of 0 to 100° C., preferably 10 to 60° C., and more preferably 15 to 35° C. The reaction time is approximately 50 hours although it varies with the scale.

The alcoholic hydroxyl-containing compounds thus obtained are useful as reagents for modifying organic resins and silicone resins in electronic applications.

EXAMPLE

Examples of the invention are given below by way of illustration and not by way of limitation.

Example 1

A flask equipped with a thermometer, condenser and stirrer was charged with 700 g of 2,2-bis[3-allyl-4-(glycidyloxy)phenyl]propane in 187 g of tetrahydrofuran.

Figure 2:
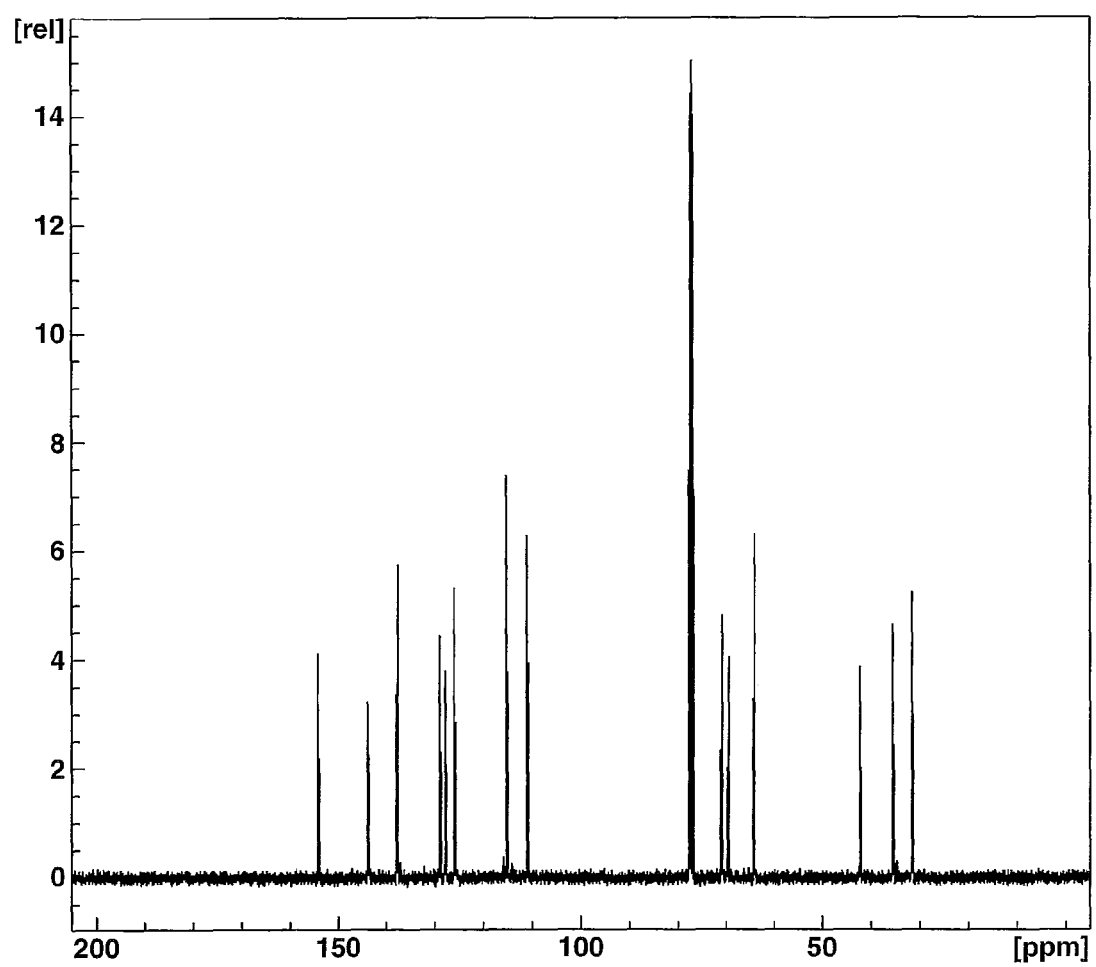

Then each 2.5 g of (R,R) and (S,S)-N,N'-bis(3,5-di-tert-butylsalicylidene)-1,2-cyclohexanediaminocobalt(II), 78 g of distilled water, and 2 g of acetic acid were added to the solution, which was stirred for 72 hours. At the end of reaction, the solvent was distilled off by heating at 85° C. in vacuum. Methanol, 395 g, was added to the residue, which was stirred for 1 hour. The precipitated catalyst solid was removed by filtration. The solvent including methanol was distilled off by heating at 85° C. in vacuum again, yielding 612 g of a reaction product as brown liquid (yield 81%). On analysis by $^1$H- and $^{13}$C-NMR spectroscopy, the reaction product was identified to be 2,2-bis[3-allyl-4-(2,3-dihydroxypropyl-oxy)phenyl]propane of the following formula (7). FIGS. 1 and 2 are $^1$H- and $^{13}$C-NMR diagrams of the compound, respectively.

(7)

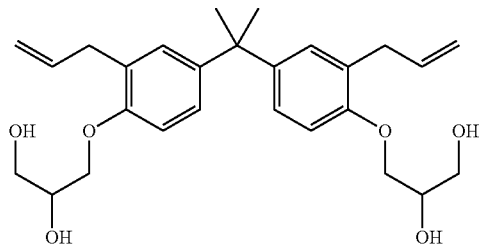

Example 2

A flask equipped with a thermometer, condenser and stirrer was charged with 80 g of 2-[2-allyl-4-(glycidyloxy)-phenyl]-2-[3-allyl-4-(glycidyloxy)phenyl]propane in 19 g of tetrahydrofuran. Then each 0.29 g of (R,R) and (S,S)-N,N'-bis(3,5-di-tert-butylsalicylidene)-1,2-cyclo-hexanediaminocobalt (II), 9.4 g of distilled water, and 0.23 g of acetic acid were added to the solution, which was stirred for 70 hours. At the end of reaction, the solvent was distilled off by heating at 85° C. in vacuum. Methanol, 120 g, was added to the residue, which was stirred for 1 hour. The precipitated catalyst solid was removed by filtration. The solvent including methanol was distilled off by heating at 85° C. in vacuum again, yielding 66 g of a reaction product as brown liquid (yield 76%). On analysis by and $^{13}$C-NMR spectroscopy, the reaction product was identified to be 2-[2-allyl-4-(2,3-dihydroxypropyloxy)phenyl]-2-[3-allyl-4-(2,3-dihydroxypropyloxy)phenyl]propane of the following formula (8).

(8)

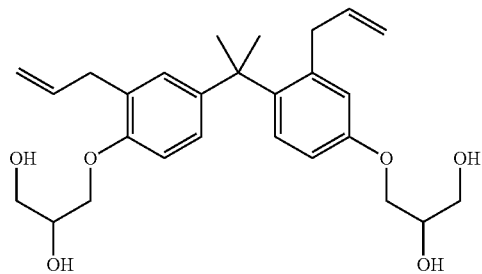

Example 3

A flask equipped with a thermometer, condenser and stirrer was charged with 78.5 g of 2,2-bis[3-allyl-4-(glycidyloxy)phenyl]propane in 22.5 g of tetrahydrofuran. Then each 0.30 g of (R,R) and (S,S)-N,N'-bis(3,5-di-tert-butylsalicylidene)-1,2-cyclohexanediaminocobalt(II), 9.4 g of distilled water, and 0.24 g of acetic acid were added to the solution, which was stirred for 72 hours. At the end of reaction, the solvent was distilled off by heating at 85° C. in vacuum. Methanol, 120 g, was added to the residue, which was stirred for 1 hour. The precipitated catalyst solid was removed by filtration. The solvent including methanol was distilled off by heating at 85° C. in vacuum again, yielding 74.1 g of a reaction product as brown liquid (yield 87%). On analysis by $^1$H- and $^{13}$C-NMR spectroscopy, the reaction product was identified to be 2,2-bis[3-allyl-4-(2,3-dihydroxypropyl-oxy)phenyl]propane of the following formula (9).

(9)

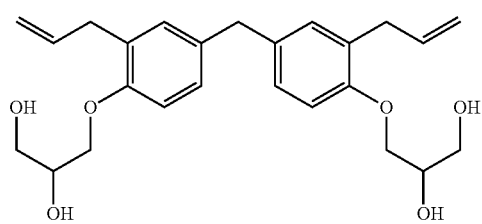

Example 4

A flask equipped with a thermometer, condenser and stirrer was charged with 10.6 g of 2,2-bis[3-allyl-4-(glycidyloxy)phenyl]hexafluoropropane in 2.3 g of tetrahydrofuran. Then each 31 mg of (R,R) and (S,S)-N,N'-bis(3,5-di-tert-butylsalicylidene)-1,2-cyclo-hexanediaminocobalt(II), 1.0 g of distilled water, and 24 mg of acetic acid were added to the solution, which was stirred for 72 hours. At the end of reaction, the solvent was distilled off by heating at 85° C. in vacuum. Methanol, 10 g, was added to the residue, which was stirred for 1 hour. The precipitated catalyst solid was removed by filtration. The solvent including methanol was distilled off by heating at 85° C. in vacuum again, yielding 9.2 g of a reaction product as brown liquid (yield 81%). On analysis by $^1$H- and $^{13}$C-NMR spectroscopy, the reaction product was identified to be 2,2-bis[3-allyl-4-(2,3-dihydroxypropyloxy) phenyl]hexafluoro-propane of the following formula (10).

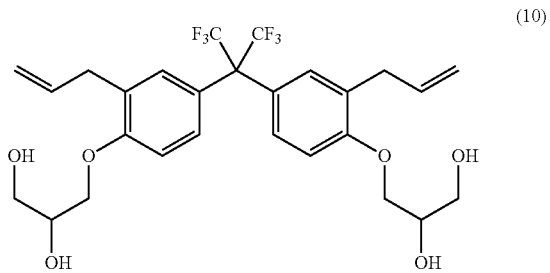

(10)

Japanese Patent Application No. 2009-232294 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An alcoholic hydroxyl-containing compound having the general formula (1):

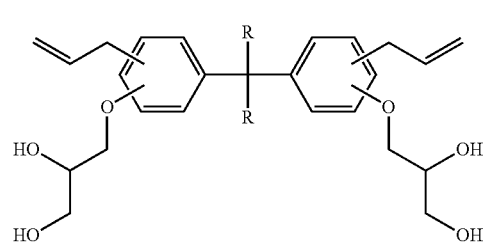

(1)

wherein R is hydrogen, methyl or trifluoromethyl.

2. A method for preparing the alcoholic hydroxyl-containing compound of claim 1, comprising the step of reacting a bisphenol derivative having the general formula (2):

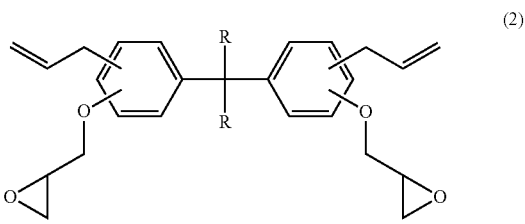

(2)

wherein R is hydrogen, methyl or trifluoromethyl with water in the presence of a transition metal catalyst having the general formula (3):

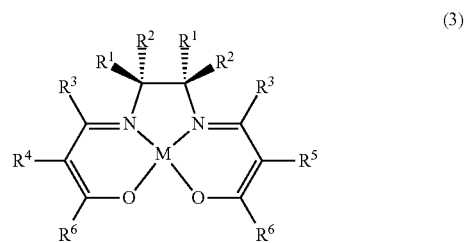

(3)

wherein $R^1$ and $R^2$ are hydrogen, alkyl or aryl, may have a substituent, or two $R^1$ or two $R^2$ may bond together to form a ring with the carbon atoms to which they are attached, $R^3$, $R^4$, $R^5$ and $R^6$ are hydrogen, alkyl or aryl, $R^4$ and $R^5$ may also be a polymer like hydroxymethylpolystyrene or silica gel, $R^6$ may form an optionally substituted ring with adjacent $R^4$ or $R^5$ and the carbon atoms to which they are attached, and M is selected from the group consisting of manganese, iron, cobalt, zinc, nickel, aluminum, chromium, ruthenium, rhodium, titanium, vanadium, molybdenum, and tungsten.

* * * * *